(12) United States Patent
Pham et al.

(10) Patent No.: US 8,920,416 B2
(45) Date of Patent: Dec. 30, 2014

(54) MEDICAL PROBE WITH TRANSLATABLE CO-ACCESS CANNULA

(75) Inventors: Francis Pham, West Chester, OH (US); Kimbolt Young, Newtonville, MA (US); Daniel Goldberg, Sylvania, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1095 days.

(21) Appl. No.: 12/892,727

(22) Filed: Sep. 28, 2010

(65) Prior Publication Data
US 2011/0077644 A1 Mar. 31, 2011

Related U.S. Application Data

(60) Provisional application No. 61/247,486, filed on Sep. 30, 2009.

(51) Int. Cl.
*A61B 18/14* (2006.01)
*A61B 18/00* (2006.01)

(52) U.S. Cl.
CPC ..... *A61B 18/1477* (2013.01); *A61B 2018/1432* (2013.01); *A61B 2018/143* (2013.01); *A61B 2018/00053* (2013.01); *A61B 2018/00577* (2013.01)
USPC .......................................................... 606/41

(58) Field of Classification Search
CPC .. A61B 18/14; A61B 18/1477; A61B 18/148; A61B 18/1482; A61B 18/1485; A61B 18/1487; A61B 2018/0016; A61B 2018/00267; A61B 2018/143; A61B 2018/1432; A61B 2018/1475
USPC .............................................. 606/41, 42, 48
See application file for complete search history.

(56) References Cited

U.S. PATENT DOCUMENTS

| | | | |
|---|---|---|---|
| 5,989,196 A | 11/1999 | Chu et al. |
| 6,379,353 B1 | 4/2002 | Nichols |
| 6,425,887 B1 | 7/2002 | McGuckin et al. |
| 6,743,226 B2 | 6/2004 | Cosman et al. |
| 6,970,742 B2 | 11/2005 | Mann et al. |
| 6,983,179 B2 | 1/2006 | Ben-Haim |

(Continued)

OTHER PUBLICATIONS

PCT International Preliminary Report on Patentability (Chapter I of the Patent Cooperation Treaty) for PCT/US2010/050576, Applicant: Boston Scientific Scimed, Inc., Form PCT/IB/326 and 373, dated Apr. 12, 2012 (10pages).

(Continued)

*Primary Examiner* — Michael Peffley
*Assistant Examiner* — Khadijeh Vahdat
(74) *Attorney, Agent, or Firm* — Kacvinsky Daisak Bluni PLLC

(57) ABSTRACT

The tissue ablation device includes a tissue ablation probe having an elongated probe shaft and electrodes carried by the distal end of the probe shaft. The device further comprises a cannula with a central lumen extending along a longitudinal axis for removably receiving the probe shaft. The cannula further comprises concentric inner and outer tubes extending along the longitudinal axis, wherein the outer is tube is translatable relative to the inner tube. The inner and outer tubes further comprise inner and outer apertures, respectively, that are aligned by translating the outer tube. When the inner and outer apertures are aligned, electrodes are deployed through the inner and outer apertures. One method includes introducing a cannula and a tissue ablation probe to a tissue site and operating the tissue ablation probe and the cannula to deploy the electrodes and ablate tissue.

17 Claims, 11 Drawing Sheets

(56) References Cited

U.S. PATENT DOCUMENTS

| | | |
|---|---|---|
| 7,229,431 B2 | 6/2007 | Houser et al. |
| 7,387,628 B1 | 6/2008 | Behl et al. |
| 2002/0022864 A1 | 2/2002 | Mahvi et al. |
| 2002/0107515 A1 | 8/2002 | Edwards et al. |
| 2003/0195502 A1* | 10/2003 | Garabedian et al. ............ 606/41 |
| 2004/0236289 A1 | 11/2004 | Ferguson et al. |
| 2005/0080409 A1* | 4/2005 | Young et al. .................... 606/41 |
| 2005/0234443 A1 | 10/2005 | Rioux et al. |
| 2006/0084965 A1* | 4/2006 | Young ............................. 606/41 |
| 2006/0095029 A1* | 5/2006 | Young et al. .................... 606/41 |
| 2006/0149226 A1 | 7/2006 | McCullagh et al. |
| 2007/0203486 A1* | 8/2007 | Young ............................. 606/41 |
| 2008/0255553 A1 | 10/2008 | Young et al. |
| 2008/0269739 A1* | 10/2008 | Young et al. .................... 606/48 |
| 2009/0198232 A1* | 8/2009 | Young et al. .................... 606/41 |

OTHER PUBLICATIONS

PCT International Search Report for PCT/US2010/050576, Applicant: Boston Scientific Scimed, Inc., Form PCT/ISA/210 and 220, dated Dec. 7, 2010 (5pages).

PCT Written Opinion of the International Search Authority for PCT/US2010/050576, Applicant: Boston Scientific Scimed, Inc., Form PCT/ISA/237, dated Dec. 7, 2010 (8pages).

* cited by examiner

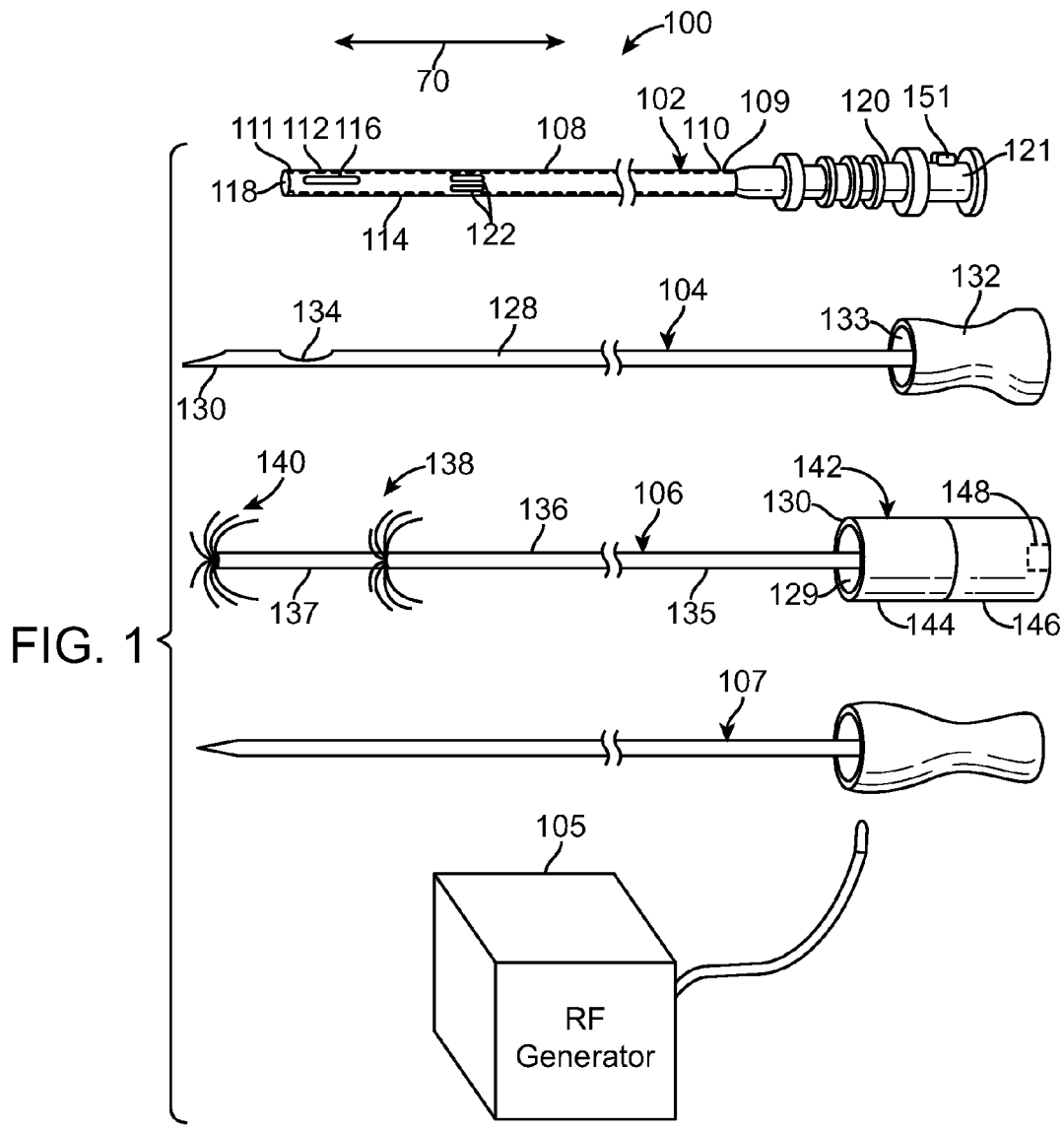
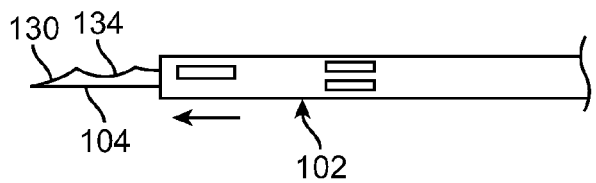
FIG. 2

MEDICAL PROBE WITH TRANSLATABLE CO-ACCESS CANNULA

RELATED APPLICATION DATA

The present application claims the benefit under 35 U.S.C. §119 to U.S. provisional patent application Ser. No. 61/247,486, filed Sep. 30, 2009. The foregoing application is hereby incorporated by reference into the present application in its entirety.

FIELD OF THE INVENTION

The field of the invention relates generally to the structure and use of cannulae and probes for the ablation of tissue.

BACKGROUND OF THE INVENTION

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from an exposed, uninsulated portion of the electrode. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a cannula and an electrode deployment member reciprocatably mounted within the delivery cannula to alternately deploy an electrode array from the cannula and retract the electrode array within the cannula. Using either of the two technologies, the energy that is conveyed from the electrode(s) translates into ion agitation, which is converted into heat and induces cellular death via coagulation necrosis. The ablation probes of both technologies are typically designed to be percutaneously introduced into a patient in order to ablate the target tissue.

In the design of such ablation probes, which may be applicable to either of the two technologies, RF energy is often delivered to an electrode located on a distal end of the probe's shaft via the shaft itself. This delivery of RF energy requires the probe to be electrically insulated to prevent undesirable ablation of healthy tissue. In the case of a single needle electrode, all but the distal tip of the electrode is coated with electrically insulative material in order to focus the RF energy at the target tissue located adjacent the distal tip of the probe. In the case of a LeVeen Needle Electrode™, RF energy is conveyed to the needle electrodes through the inner electrode deployment member, and the outer cannula is coated with an electrically insulative material to prevent RF energy from being transversely conveyed from the inner electrode deployment member along the length of the probe.

RF energy is commonly delivered to the electrode element of a tissue ablation probe (whether a single needle electrode or needle electrode array, deployable or otherwise) and thus to tissue in one of several ways. In one arrangement, RF current is delivered to an ablation electrode element in a monopolar fashion, wherein current passes from the ablation electrode element to a dispersive electrode attached externally to the patient, such as a contact pad placed on the patient's flank. In another arrangement, the RF current is delivered to two electrodes in a bipolar fashion, wherein current passes between "positive" and "negative" electrodes in close proximity to each other, e.g., two electrodes on the same probe or array or on different probes or arrays. Bipolar arrangements require the RF energy to traverse through a relatively small amount of tissue between the tightly spaced electrodes and are generally more efficient than monopolar arrangements, which require the RF energy to traverse through the thickness of the patient's body. Thus, bipolar ablation probes generally create larger and/or more efficient lesions than monopolar ablation probes. Additionally, bipolar arrangements are generally safer for the physician and patient, since the monopolar arrangement presents the risk that the physician and patient may become a ground in the monopolar arrangement, resulting in painful burns.

Currently, bipolar LeVeen-type ablation probes comprising two axially arranged deployable electrode arrays (a proximal electrode array and a distal electrode array) combine the advantages that accompany the use of electrode arrays and bipolar ablation. Details regarding the structure and operation of such bipolar ablation probes are disclosed in U.S. Patent Publication 2002/0022864, entitled "Multipolar Electrode System for Radiofrequency Ablation," and U.S. patent application Ser. No. 09/663,048, entitled "Methods and Systems for Focused Bipolar Tissue Ablation," both of which are expressly incorporated herein by reference.

In a typical tumor diagnostic and therapeutic procedure, tissue suspected of containing an abnormality is imaged using a high definition imaging modality, such as Magnetic Resonance Imaging (MRI). If an abnormality, such as a tumor, is discovered, a sample of the abnormal tissue may be retrieved by percutaneously introducing a biopsy needle through healthy tissue into contact with the abnormal tissue to obtain a tissue sample for laboratory analysis. The treating physician may further proceed with treating the tumor immediately after performing the biopsy, or after analysis of the malignancy indicates further treatment is needed.

In either case, the tumor can be treated by percutaneously introducing an RF ablation probe through the patient's body to contact the tumor in a similar manner as the biopsy needle described above. The ablation probe can then be operated to ablate the tumor, after which the ablated region can be treated with a therapeutic agent, such as a drug. This may be accomplished by introducing a separate drug delivery device into the ablated region in the same manner as the biopsy needle and ablation probe.

In performing the diagnostic/therapeutic procedure, the biopsy stylet, RF ablation probe, and drug delivery device can either be percutaneously introduced into the patient's body as stand-alone devices or as parts of a co-access delivery system. In the former case, each device may follow a different path than the devices before it, and thus must be meticulously delivered to the targeted region in the patent's body under an imaging modality, such as fluoroscopy and/or CT. The multiple tissue insertions also increase the pain and discomfort suffered by the patient during this procedure. When a co-access delivery system is used, however, each device is delivered through a single cannula that advantageously provides a more accurate delivery of the devices to the targeted region. That is, after the biopsy stylet has been delivered through the cannula and a biopsy is taken from the center of the targeted region, the cannula provides a convenient place marker for subsequent delivery of the ablation probe and drug delivery device to the targeted region without the need for navigational imaging. The use of a co-access delivery system also only requires a single percutaneous insertion, i.e., insertion of the cannula.

In some co-access system models, the cannula includes an axial opening on the distal end in addition to side slots through which one or more electrode arrays may deploy. However, the side slots typically remain in an open configuration. Thus, if a user wishes to deliver a substance, such as a pharmaceutical agent, through the open distal end of the cannula to a small, targeted tissue area, the substance may leak out of the side slots. This prevents accurate delivery of the pharmaceutical agent. Also, when it is desired to deliver a pharmaceutical agent to different regions of target tissue, the open slots and the open distal end cause difficulty in selecting and delivering the pharmaceutical agent to multiple select areas.

Therefore, there is a need in the art for a co-access ablation probe that allows multiple electrodes to be properly deployed, while also allowing for proper placement of other medical elements, within a treatment region of a patient.

SUMMARY OF THE INVENTION

In accordance with one aspect of the present inventions, a tissue ablation device is provided. The tissue ablation device comprises an ablation probe with an elongated probe shaft having a proximal end, a distal end, and a plurality of electrodes carried on the shaft distal end. The device also includes a cannula with an elongated cannula shaft having a proximal end, a distal end, and concentric inner and outer tubes extending along a common longitudinal axis, wherein the outer tube is translatable relative to the inner tube. A lumen extends longitudinally within the cannula shaft between the proximal and distal ends and is configured for removably receiving the probe shaft.

A plurality of inner apertures is disposed transversely through a wall of the inner tube and are in communication with the cannula lumen, and a plurality of outer apertures are disposed transversely through a wall of the outer tube. The inner apertures may be located on a distal end of the inner tube and the outer apertures may be located on a distal end of the outer tube. The outer tube is selectively translatable to align and misalign the plurality of outer apertures with the plurality of inner apertures. In one embodiment, the outer tube is rotationally translatable relative to the inner tube, and in an alternative embodiment, the outer tube is longitudinally translatable relative to the inner tube. When the inner and outer apertures are aligned, at least one of the plurality of electrodes is deployable through at least one of the aligned inner and outer apertures.

In one embodiment, the plurality of electrodes includes a proximal electrode array and a distal electrode array. In this embodiment, the plurality of apertures comprises proximal inner and outer apertures and distal inner and outer apertures, wherein the proximal electrode array is deployable through the aligned proximal inner and outer apertures, and the distal electrode array is deployable through the aligned distal inner and outer apertures. In an alternative embodiment, the cannula outer tube comprises a proximal portion and a distal portion, wherein the proximal portion and the distal portion are separately translatable. The proximal portion is translatable to align the proximal inner and outer apertures, and the distal portion is translatable to align the distal inner and outer apertures.

The tissue ablation device may include a handle assembly carried on the proximal end of the probe shaft. The handle assembly includes an electrical port coupling the plurality of electrodes to a source of electrical energy. In one embodiment, the electrical energy is RF energy.

In a method of using the tissue ablation device to ablate target tissue, the cannula is introduced to a tissue site, and the probe is distally slid through the cannula lumen. The cannula outer tube is translated such that the plurality of inner and outer apertures are aligned, and at least one of the plurality of electrodes is deployed through at least one of the aligned inner and outer apertures. The probe is then operated to ablate tissue by delivering electrical energy from the plurality of electrodes to the tissue site.

In another method, a substance, such as a pharmaceutical agent is delivered through the cannula lumen. The inner and outer apertures may be misaligned prior to delivering the medical element through the cannula lumen, such that the substance is delivered through an axial opening on the distal end of the cannula shaft. In yet another method, the inner and outer apertures are aligned prior to delivering the substance through the cannula lumen, such that the substance is delivered through the inner and outer apertures and an axial opening on the distal end of the cannula shaft.

In yet another method, the plurality of electrodes comprises a proximal array of electrodes and a distal array of electrodes, and the method further comprises translating a proximal portion of the outer tube separately from a distal portion of the outer tube to align a proximal portion of the outer apertures with a proximal portion of the inner apertures, and deploying the proximal array of electrodes through the proximal portion of aligned inner and outer apertures. The method may further comprise translating a distal portion of the outer tube separately from the proximal portion of the outer tube to align a distal portion of the outer apertures with a distal portion of the inner apertures, and deploying the distal array of electrodes through the distal portion of aligned inner and outer apertures.

In another method, a substance is introduced in the cannula lumen prior to alignment of the inner and outer apertures, and the substance is delivered through the aligned inner and outer apertures.

In yet another method, a cannula is introduced to a tissue site, wherein the cannula has a shaft with concentric inner and outer tubes each having a plurality of apertures, wherein the inner and outer tubes are translatable relative to each other. The cannula also has a lumen extending longitudinally within the cannula shaft in communication with the plurality of apertures of the inner tube. The method also includes distally sliding a probe shaft through the cannula lumen, wherein the probe shaft has at least one electrode array. The cannula outer tube is translated such that the plurality of inner and outer apertures are aligned, and the at least one electrode array is deployed through at least one of the aligned inner and outer apertures. The probe is operated to ablate tissue by delivering electrical energy from the at least one electrode array to the tissue.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is a plan view of a tissue treatment device arranged in accordance with one preferred embodiment of the present inventions, wherein a delivery cannula, biopsy stylet, ablation probe, and obturator are particularly shown;

FIG. 2 is a side view of the combination of the delivery cannula and stylet of FIG. 1;

DETAILED DESCRIPTION OF THE EMBODIMENTS

Figure 3:
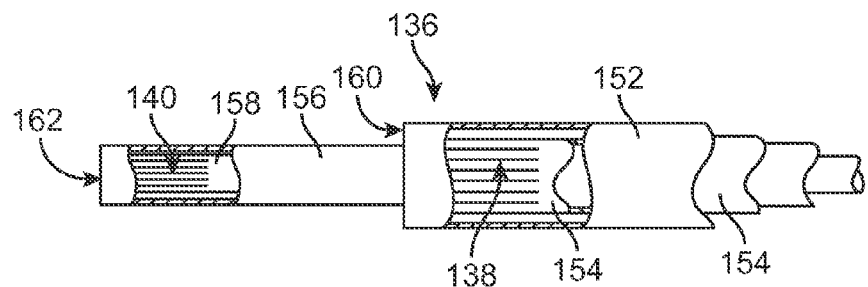
FIG. 3 is a partially cutaway side view of the distal end of the ablation probe of FIG. 1, wherein retracted electrode arrays are particularly shown.

FIG. 1 illustrates a tissue treatment device 100 arranged in accordance with a preferred embodiment of the present invention. The tissue treatment device 100 generally comprises a delivery cannula 102 that can be percutaneously introduced within a patient, a biopsy stylet 104 configured for removing a tissue sample from the patient, and an ablation probe 106 configured for therapeutically ablating tissue. The biopsy stylet 104 and ablation probe 106 are configured to be alternately introduced through the delivery cannula 102 in contact with the tissue to be treated. The tissue treatment device 100 may optionally comprise an obturator 107 configured for facilitating the percutaneous introduction of the delivery cannula 102 into the patient's body. The tissue treatment device 100, and in particular, the ablation probe 106, is configured to be used with an radio frequency (RF) generator 105, as will be described in further detail below.

The biopsy stylet 104 comprises a solid elongated shaft 128 with a tissue-penetrating distal tip 130 and a proximal handle 132. The handle 132 is preferably composed of a durable and rigid material, such as medical grade plastic, and is ergonomically molded to allow a physician to more easily manipulate the shaft 128. The handle 132 also comprises a distally facing female connector 133 configured to mate with the cannula 102 to form an integrated assembly. The biopsy stylet 104 may be operated in a standard manner to obtain a tissue sample. For example, in the illustrated embodiment, the biopsy stylet 104 comprises a grooved notch 134 just proximal to the distal tip 130. Referring to FIG. 2, when the stylet 104 is advanced from the delivery cannula 102 to expose the notch 134, the tissue prolapses into the notch 134, and then the delivery cannula 102 can be advanced, thereby shearing the tissue to sever the sample. The sample is held protected inside the notch 134. The stylet 104 can then be removed from the cannula lumen 114 in order to retrieve the tissue sample. Further details regarding the structure and use of biopsy stylets in association with cannulae are disclosed in U.S. Pat. No. 5,989,196, which is expressly incorporated herein by reference.

Referring back to FIG. 1, the ablation probe 106 generally comprises a rigid coaxial probe shaft 136 having a proximal end 135 and a distal end 137. For the purposes of this specification, a shaft is rigid if it is generally not suitable to be advanced along a tortuous anatomical conduit of a patient, as contrasted to, e.g., guidewires and intravascular catheters. The probe shaft 136 has a suitable length, typically in the range of 5 cm to 30 cm, preferably from 10 cm to 20 cm. The probe shaft 136 has an outside diameter consistent with its intended use. In the illustrated embodiment, the probe shaft 136 has sufficient columnar strength, such that the components of the probe shaft 136 can be more easily moved relative to each other.

The probe 106 further includes one or more electrodes configured to be deployed from the distal end 137 of the probe shaft 136, which may include a first or proximal electrode array 138 and a second or distal electrode array 140, as illustrated in FIG. 1. The ablation probe 106 includes a handle assembly 142 mounted to the proximal end 135 of the probe shaft 136. The handle assembly 142 is preferably composed of a durable and rigid material, such as medical grade plastic, and is ergonomically molded to allow a physician to more easily manipulate the probe shaft 136. The handle assembly 142 comprises a distal handle member 144 and a proximal handle member 146 slidably engaged within the distal handle member 144. As will be described in further detail below, the distal handle member 144 can be moved relative to the proximal handle member 146 to alternately deploy the proximal and distal electrode arrays 138, 140 out from the probe shaft 136 and retract the proximal and distal electrode arrays 138, 140 within the probe shaft 136. The proximal handle member 146 also comprises an electrical connector 148 (shown in phantom), which electrically couples the RF generator 105 to the electrodes 138, 140 as will be described in further detail below. The distal handle member 144 comprises a distally facing female connector 129 configured to be mated with the cannula 102, as will be described below.

Figure 4:
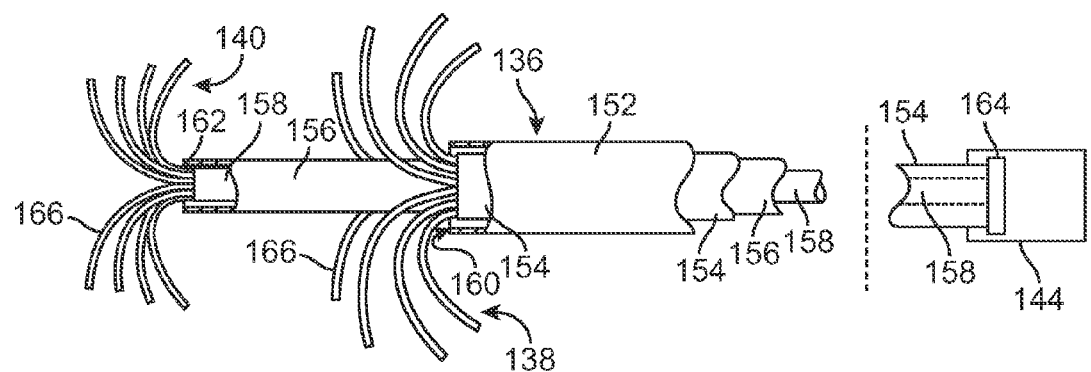
FIG. 4 is a partially cutaway side view of the distal end of the ablation probe of FIG. 1, wherein deployed electrode arrays are particularly shown.

Referring now to FIGS. 3 and 4, the probe shaft 136 comprises a proximal housing tube 152 and a proximal deployment shaft 154 on which the proximal electrode array 138 is mounted. The proximal deployment shaft 154 is configured for being reciprocatably moved within the proximal housing tube 152 to deploy the proximal electrode array 138 out from the proximal housing tube 152 (FIG. 4) and retract the proximal electrode array 138 within the proximal housing tube 152 (FIG. 3). The probe shaft 136 also comprises a distal housing tube 156 and a distal deployment shaft 158 on which the distal electrode array 140 is mounted. The distal deployment shaft 158 is configured for being reciprocatably moved within the distal housing tube 156 to deploy the distal electrode array 140 out from the distal housing tube 156 (FIG. 4) and retract the distal electrode array 140 within the distal housing tube 156 (FIG. 3). The proximal and distal electrode arrays 138, 140 can be mounted anywhere on the respective proximal and distal deployment shafts 154, 158, but preferably are mounted to the distal ends of the deployment shafts 154, 158.

The components of the probe shaft 136 and the handle assembly 142 are integrated together in a manner that allows the proximal and distal electrode arrays 138, 140 to be simultaneously deployed. In particular, the proximal and distal housing tubes 152, 156 are affixed within the distal handle member 144, with the distal housing tube 156 extending within and through the proximal housing tube 152 to form an annular window 160 between the distal end of the proximal housing tube 152 and the exterior surface of the distal housing tube 156. The distal deployment shaft 158, which extends through the distal housing tube 156, is proximally affixed to the proximal handle member 146. The proximal deployment shaft 154, which is nested between the housing tubes 152, 156, is affixed to the proximal handle member 146 via a yoke 164 reciprocatably disposed within the distal handle member 144. The yoke 164 is mounted to the distal deployment member 158, such that the proximal deployment member 154 will move with the distal deployment member 158 when the proximal handle member 146 is moved.

Thus, distal movement of the proximal handle member 146 accordingly displaces the proximal and distal deployment shafts 154, 158 relative to the proximal and distal housing tubes 152, 156, thereby deploying the proximal electrode array 138 out from the annular window 160 formed between proximal and distal housing tubes 152, 156, and deploying the distal electrode array 140 out from an axial opening 162 formed at the distal end of the distal housing tube 156. To facilitate coaxial movement between the components of the probe shaft 136, the surfaces of the proximal and distal housing tubes 152, 156, and proximal and distal deployment shafts 154, 158 can be coated with a lubricious material.

Each of the proximal and distal electrode arrays 138, 140 comprises a plurality of tines 166. Each tine 166 is a small diameter metal element, which can penetrate into tissue as it is advanced into a target site within the target region. Each tine 166 can also be formed from resilient conductive metals having a suitable shape memory. Many different metals such as stainless steel, nickel-titanium alloys, nickel-chromium alloys, and spring steel alloys can be used for this purpose. The tines 166 may have circular or non-circular cross-sections, but preferably have rectilinear cross-sections. When constructed in this fashion, the tines 166 are generally stiffer in the transverse direction and more flexible in the radial direction. The circumferential alignment of the tines 166 within the probe shaft 136 can be enhanced by increasing transverse stiffness. Exemplary tines will have a width in the circumferential direction in the range of 0.2 mm to 0.6 mm, preferably from 0.35 mm to 0.40 mm, and a thickness, in the radial direction, in the range of 0.05 mm to 0.3 mm, preferably from 0.1 mm to 0.2 mm.

The distal ends of the tines 166 may be honed or sharpened to facilitate their ability to penetrate tissue and hardened using conventional heat treatment or other metallurgical processes. The tines 166 may be partially covered with insulation, although they will be at least partially free from insulation over their distal ends. The proximal ends of the tines 166 may be directly coupled to the electrical connector 148 located on the proximal handle member 146, or alternatively indirectly coupled thereto via other intermediate conductors, such as RF wires (not shown). Optionally, the deployment shafts 154, 158 and any component are composed of an electrically conductive material, such as stainless steel, and may therefore conveniently serve as intermediate electrical conductors. If the deployment shafts 154, 158 do serve as conductors, the outer surfaces of the deployment shafts 154, 158, and/or the inner surfaces of the housing tubes 152, 156 are coated with a suitable electrically insulative material.

As illustrated in FIG. 3, the electrode arrays 138, 140 are placed in a radially collapsed configuration when retracted within the respective housing tubes 152, 156, with each tine 166 constrained and held in a generally axially aligned position within the probe shaft 136 to facilitate its introduction into the tissue target site. As illustrated in FIG. 4, the electrode arrays 138, 140 are placed in a three-dimensional umbrella-shaped configuration that usually defines a generally spherical or ellipsoidal volume having a periphery with a maximum radius in the range of 0.5 cm to 4 cm. The tines 166 are resilient and pre-shaped to assume a desired configuration when advanced into tissue. In the illustrated embodiment, the tines 166 diverge radially outwardly from the probe shaft 136 in a uniform pattern, i.e., with the spacing between adjacent tines 166 diverging in a substantially uniform pattern or symmetric pattern or both. In the illustrated embodiment, the tines 166 evert proximally, so that they face partially or fully in the proximal direction when fully deployed. In exemplary embodiments, pairs of adjacent tines 166 can be spaced from each other in similar or identical, repeated patterns that can be symmetrically positioned about an axis of the inner probe shaft 136.

Figure 5:
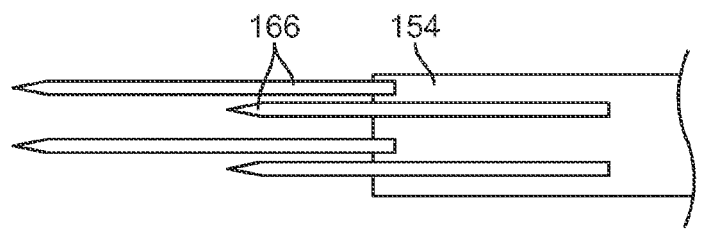
FIG. 5 is a cutaway side view of the distal end of an alternative embodiment of a deployment shaft used to deploy a proximal electrode array from the ablation probe of FIG. 1.

It will be appreciated by one of ordinary skill in the art that a wide variety of patterns can be used to uniformly cover the region to be treated. It should be noted that while eight tines 166 for each array 138, 140 are illustrated in FIG. 4, the number of tines 166 can vary based on the total circumferential distance available. Thus, the tines 166 could be more tightly packed or more widely spaced. As briefly discussed above, the tines 166 of each electrode array 138, 140 are longitudinally aligned along the probe shaft 136. Alternatively, as illustrated in FIG. 5, the tines 166 of the proximal electrode array 138 are shown to be staggered, thereby minimizing the profile of the ablation probe 106 and facilitating mounting of the proximal electrode array 138 to the proximal deployment shaft 154. The electrodes 138, 140 may also have other configurations, such as arrays with straight tines oriented proximally or distally relative to the probe shaft 136. The electrodes 138, 140 may also include three or more arrays, or a single electrode tine. Further details regarding electrode array-type probe arrangements are disclosed in U.S. Pat. No. 6,379,353, which is incorporated herein by reference.

Although the proximal and distal electrode arrays 138, 140 are shown in the illustrated embodiment as facing or deploying in the same direction, it should be noted that the electrode arrays 138, 140 can be made to face or deploy in opposite directions. The electrode arrays 138, 140 can also be made to independently deploy, rather than simultaneously deploy. Further details regarding these alternative features, as well as other electrode deployment mechanisms, are described in U.S. patent application Ser. No. 09/663,048, entitled "Methods and Systems for Focused Bipolar Tissue Ablation," which has previously been incorporated herein by reference.

In one embodiment, the proximal and distal electrode arrays 138, 140 are in a bipolar arrangement. Thus, when RF energy is conveyed to the ablation probe 12, the RF current passes between the arrays 138, 140, i.e., between a positive one of the arrays and a negative one of the arrays, thereby concentrating the energy flux in order to have an injurious effect on the tissue between or substantially adjacent to the proximal and distal electrode arrays 138, 140. In this bipolar arrangement, the arrays 138, 140 should be electrically insulative from each other. For example, the electrode arrays 138, 140 may be coupled to the RF generator 105 via separate wires (not shown).

In an alternative embodiment, the proximal and distal electrode arrays 138, 140 are in a monopolar arrangement. In this embodiment, the current passes from the proximal and distal electrode arrays 138, 140, which are configured to concentrate the energy flux in order to have an injurious effect on the surrounding tissue, to a dispersive electrode (not shown) located remotely from the electrode arrays 138, 140. The dispersive electrode may be attached externally to the patient, e.g., using a contact pad placed on the patient's flank, and has a sufficiently large area (typically 130 cm$^2$ for an adult), such that the current density is low and non-injurious to surrounding tissue.

Referring back to FIG. 1, the cannula 102 includes an elongate shaft 108 having a proximal end 109, a distal end 111, and a central lumen 114 (shown in phantom) extending between the proximal end 109 and the distal end 111 along a longitudinal axis 70. The cannula shaft 108 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm. The central lumen 114 is sized such that the probe shaft 136 may be slid in and out of the central lumen 114.

The cannula shaft 108 may be rigid, semi-rigid, or flexible, depending upon the designed means for introducing the delivery cannula 102 to the target tissue. In the preferred embodiment, the cannula shaft 108 is composed of an electrically conductive material, such as stainless steel. In this case, the exterior surface of the cannula shaft 108 is preferably composed of an electrically insulative material. Alternatively, a substantial portion of or the entire cannula shaft 108 may be composed of an electrically insulative material, such as a medical grade plastic, in which case, a separate insulative coating is not needed.

In the illustrated embodiment, the cannula shaft 108 has a blunt distal tip that is not capable of being percutaneously introduced into a patient's body by itself. To facilitate percutaneous introduction of the delivery cannula 102 through tissue, the optional obturator 107 takes the form of a conventional trocar 107, which can be introduced through the cannula lumen 114. In this manner, the trocar 107 serves to prevent tissue from entering the axial opening 118 at the distal end 111 of the cannula shaft 108, while providing a tissue penetrating tip for facilitating introduction of the delivery cannula 102 through solid tissue. The use of the trocar 107 provides axial rigidity to the delivery cannula 102, which allows the cannula shaft 108 to be composed of a flexible material if desired and/or to be fabricated with a thinner wall, resulting in a lower profile. Alternatively, the cannula shaft 108 may have a sharpened tissue penetrating tip, in which case, a blunt-nosed obturator may be used to prevent tissue coring.

The distal end 111 of the cannula shaft 108 preferably carries a visualization marker 116 to allow the physician to identify the orientation and/or the depth in the delivery site of the delivery cannula 102. The visualization marker 116 may be an ultrasound, MRI or other visualization marker known to those of skill in the art. The delivery cannula 102 may also feature a series of markings, similar to a ruler, as an additional means of visualizing the depth of the delivery cannula 102.

The cannula lumen 114 terminates at an axial opening 118 located at the distal tip of the cannula shaft 108. As will be described in further detail below, the axial opening 118 serves as a port out which respective operative elements of the biopsy stylet 104 or any pharmaceutical agents are delivered to a targeted tissue region.

The delivery cannula 102 further comprises a proximal adapter 120 mounted to the proximal end 110 of the cannula shaft 108. The proximal adapter 120 is preferably composed of a durable and rigid material, such as medical grade plastic. The proximal adapter 120 is configured to mate with the stylet 104 and ablation probe 106 to form an integrated assembly. To this end, the proximal adapter 120 comprises a proximally facing male connector piece 121 sized to slide within respective female connectors located on the selected stylet 104 and ablation probe 106. The proximal adapter 120 may optionally comprise an electrical connector and/or fluid delivery port (both not shown), so that the delivery cannula 102 can be used as a separate means of delivering ablation energy to chemotherapeutic agents to tissue. Further details regarding these optional features are described in U.S. patent application Ser. No. 10/828,032, entitled "Co-Access Bipolar Ablation Probe"), which is expressly incorporated herein by reference. As will be described in further detail below, the biopsy stylet 104, ablation probe 106, and optional chemotherapeutic agents can be interchangeably introduced into the cannula lumen 114.

Significantly, the cannula shaft 108 includes an inner tube and an outer tube in a concentric arrangement, wherein the outer tube is translatable relative to the inner tube to thereby alternately align and misalign apertures located on the inner tube and outer tube, as will be described in further detail below. Translation of the inner and outer tubes can be accomplished in one of several different manners.

Figure 6A:
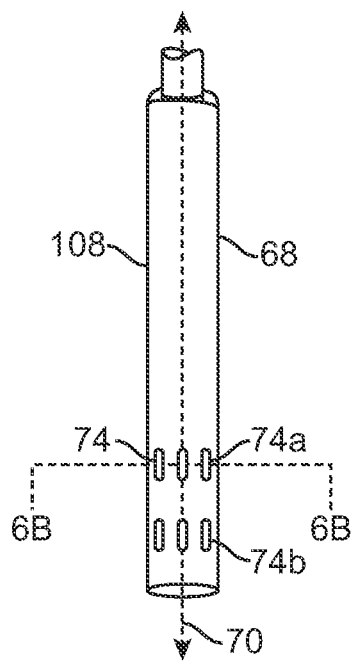
FIG. 6A is a side view of the embodiment of the ablation probe and cannula shown in FIG. 1.
Figure 6B:
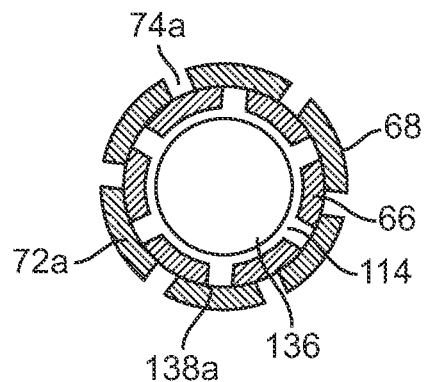
FIG. 6B is a cross-sectional view of the embodiment of the ablation probe and cannula shown in FIG. 6A taken along the line 6B-6B.
Figure 6C:
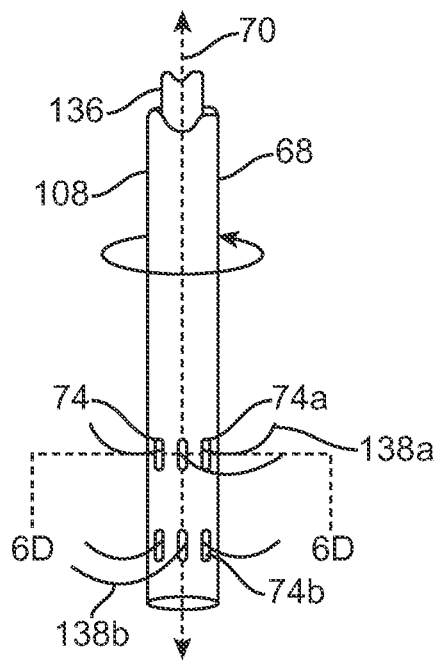
FIG. 6C is a side view of the embodiment of the ablation probe and cannula shown in FIG. 6A featuring deployment of electrode arrays.
Figure 6D:
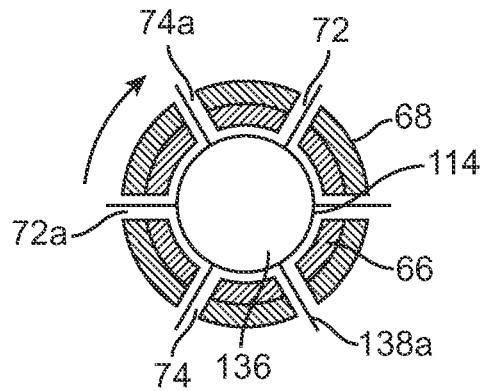
FIG. 6D is a cross-sectional view of the embodiment of the ablation probe and cannula shown in FIG. 6C taken along the line 6D-6D.

Referring to FIGS. 6A-6D, one embodiment of the cannula shaft 108 includes an inner tube 66 and an outer tube 68 in a concentric arrangement extending along the longitudinal axis 70 of the cannula shaft 108, wherein the outer tube 68 is translated by axial rotation around the longitudinal axis 70 of the cannula shaft 108 relative to the inner tube 66, such that the outer tube 68 rotates around the circumference of the inner tube 66. The inner tube 66 includes a plurality of inner apertures 72 transversely disposed through a wall of the inner tube 66 and in communication with the central lumen 64. In addition, the outer tube 68 includes a plurality of outer apertures 74 transversely disposed through a wall of the outer tube 68. The outer tube 68 is rotationally translatable relative to the inner tube 66 to alternately and selectively misalign the inner apertures 72 with the outer apertures 74, thereby placing the apertures in a closed position (FIGS. 6A and 6B), and to align the inner and outer apertures 72, 74, thereby placing the apertures in an open position (FIGS. 6C and 6D).

When the inner apertures 72 and the outer apertures 74 are aligned, the central lumen 104 is placed in communication with the area external to the cannula 102, such as a target tissue region. When one or more of the electrodes 138, 140 is deployed from the probe shaft 136, as described above, one or more of the electrodes 138, 140 is also deployed through the aligned inner and outer apertures 72, 74 (FIGS. 6C and 6D) to the target tissue region. For this reason, the inner and outer apertures 72, 74 are preferably located at or near the distal end 111 of the cannula shaft 108, since the distal end 111 is typically positioned in a target tissue region during an ablation procedure.

In the illustrated embodiment, the inner apertures 72 include proximal inner apertures 72a and distal inner apertures 72b, and the outer apertures include proximal outer apertures 74a and distal apertures 74b. The outer tube 68 may be translated to align the proximal inner apertures 72a with the proximal outer apertures 74a, and to align the distal inner apertures 72b with the distal outer apertures 74b. In this manner, when the probe 106 is operated to deploy the proximal and distal electrodes 138, 140 from the probe shaft 136, as described above, the proximal electrode 138 deploys through the aligned proximal inner and outer apertures 72a, 74a, and the distal electrode 140 deploys through the aligned distal inner and outer apertures 72b, 74b.

The position of the inner and outer apertures 72, 74 on the cannula shaft 108 preferably corresponds longitudinally and/or circumferentially to the configuration of the electrodes 138, 140 to allow for effective deployment through the inner and outer apertures 72, 74. In addition, the proximal and distal electrode arrays 138, 140 are aligned with the respective proximal and distal inner apertures 72a, 72b with a registration mechanism, and in particular a key slot (not shown), on the distal handle member 144 which is configured to engage a corresponding registration mechanism, and in particular a key 151, on the proximal adapter 120 of the delivery cannula 102 (see FIG. 1). In this manner, circumferential alignment of the electrode arrays 138, 140 with the corresponding inner apertures 72 on the delivery cannula 102 is ensured, thereby facilitating deployment of the electrode arrays 138, 140. Alternatively, other types of registration mechanisms can be provided, e.g., applying marks on the distal handle member 144 and proximal adapter 120 that can be aligned by the physician.

Preferably, the inner and outer tubes 66, 68 extend substantially the entire length of the cannula shaft 58, such that the outer tube 68 is translatable from the proximal end 109 of the cannula shaft 108. In an alternative embodiment, both the inner and outer tubes 66, 68 comprise only a distal portion of the cannula shaft 108. The outer tube 68 may be translated using an extension (not shown) on a proximal end of the outer tube 68 that may be operated when the cannula 102 is percutaneously inserted in a patient. In this embodiment, the inner and outer tubes 66, 68 may be composed of material different from the remainder of the cannula shaft 58, i.e., the proximal portion. For example, the inner and outer tubes 66, 68 may form a rigid distal portion of the cannula shaft 118 to facilitate percutaneous insertion in a patient, while the proximal portion of the cannula shaft 58 is flexible. This may facilitate maneuverability on the proximal end 109 of the cannula 102, as well as allow for introduction of the cannula 102 through vessels and other tortuous tissue channels.

Figure 7A:
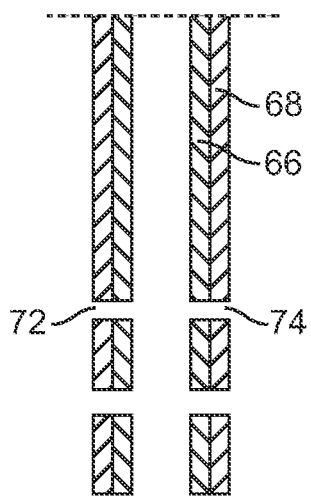
FIGS. 7A and 7B are side views of alternative embodiments of a distal end of the cannula in FIG. 1.
Figure 7B:
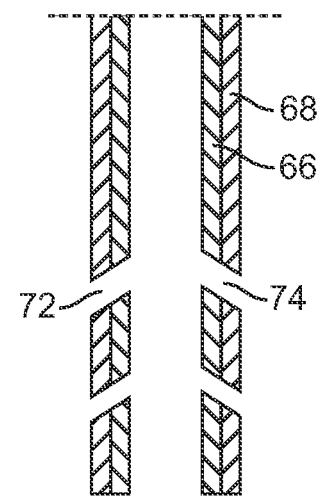

The inner and outer apertures 72, 74 may have any of a variety of configurations suitable for the type of electrodes 138, 140 or other substances to be deployed through the inner and outer apertures 72, 74. For example, the inner and outer apertures 72, 74 may be substantially circular, slotted, or other forms. The inner and outer apertures 72, 74 may also have different orientations relative to the longitudinal axis 70. For example, the inner and outer apertures 72, 74 may be oriented perpendicular to the longitudinal axis 70, as shown in FIG. 7A. Alternatively, the inner and outer apertures 72, 74 may be angled relative to the longitudinal axis 70 so the electrodes 138, 140, or other material deployed through the inner and outer apertures 72, 74, are directed to deploy in the direction of such angle, as shown in FIG. 7B. A similar configuration may also be achieved by slightly misaligning the inner and outer apertures 72, 74 to form an angled passageway, such that material is deployed through the inner and outer apertures 72, 74 at an angle relative to the longitudinal axis 70.

Figure 8A:
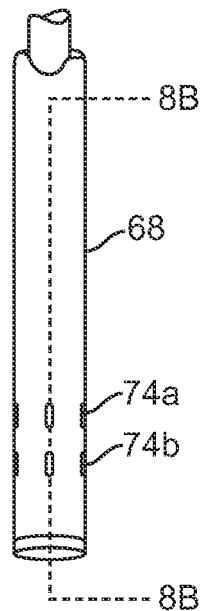
FIG. 8A is a side view of an alternative embodiment of the ablation probe and cannula shown in FIG. 1.
Figure 8B:
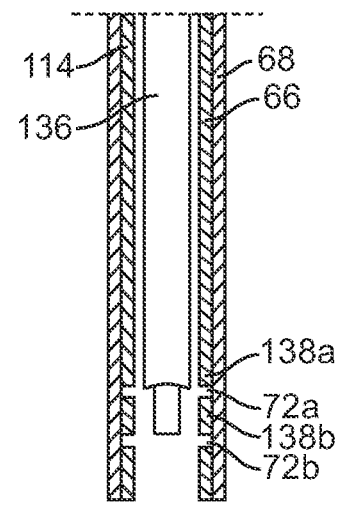
FIG. 8B is a cross-sectional view of the embodiment of the ablation probe and cannula shown in FIG. 8A taken along the line 8B-8B.
Figure 8C:
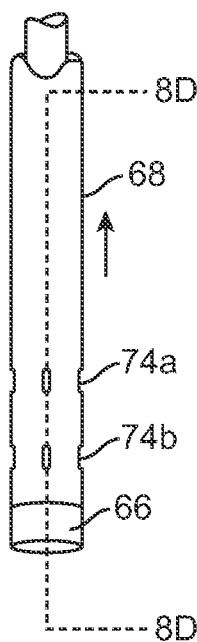
FIG. 8C is a side view of the embodiment of the ablation probe and cannula shown in FIG. 8A featuring deployment of electrode arrays.
Figure 8D:
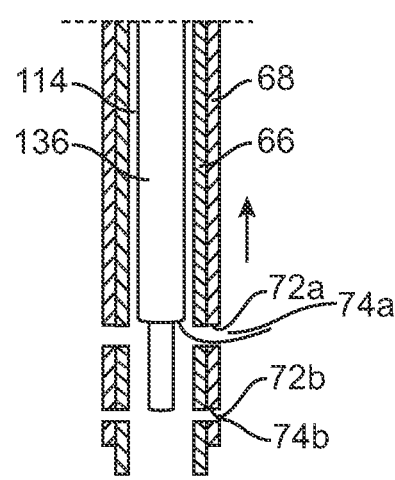
FIG. 8D is a cross-sectional view of the embodiment of the ablation probe and cannula shown in FIG. 8C taken along the line 8D-8D.

Referring to FIGS. 8A-8D, the inner tube 66 and the outer tube 68 in an alternative embodiment are in a concentric arrangement extending along the longitudinal axis 70, wherein the outer tube 68 is longitudinally translatable along the axis 70 relative to the inner tube 66. Similar to embodiment shown in FIGS. 6A-6D, the proximal inner apertures 72 are on a distal end of the inner tube 66, and the outer apertures 68 are on a distal end of the outer tube 68. Also, the inner apertures 72 include proximal inner apertures 72a and distal inner apertures 72b, and the outer apertures 74 include proximal outer apertures 72a and distal outer apertures 72b. In one embodiment, the outer tube 68 is distally translatable relative to the inner tube 66 to alternately and selectively misalign the inner apertures 72 with the outer apertures 74, thereby placing the apertures in a closed position (FIGS. 8A and 8B). The outer tube 68 is proximally translatable to align the inner and outer apertures 72, 74, thereby placing the apertures in an open position (FIGS. 8C and 8D).

Figure 9A:
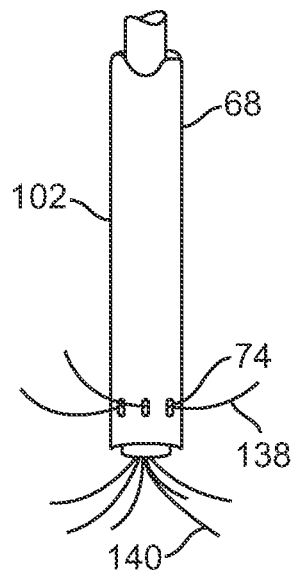
FIGS. 9A and 9B are side views of an alternative embodiment of the ablation probe and cannula in FIG. 1.
Figure 9B:
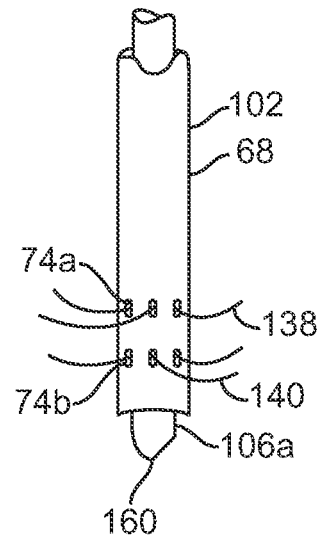

In yet another embodiment, in addition to being deployed through the inner and outer apertures 72, 74, one or more of the electrodes 138, 140 may also be deployed through the axial end 118 of the cannula 102. For example, the distal electrode array 140 may be deployed through the axial opening 118, while the proximal electrode array 138 is deployed through the aligned inner and outer apertures 72, 74, as shown in FIG. 9A. In an alternative, embodiment, an ablation probe 106a includes proximal and distal electrode arrays 138, 140 and a distal tip 160 that extends beyond the proximal electrode array 140 on the probe shaft 136, as shown in FIG. 9B. The proximal and distal electrode arrays 138, 140 are respectively deployable through the proximal inner and outer apertures 72a, 74a and the distal inner and outer apertures 72b 74b. In addition, the distal tip 160 is deployable through the axial opening 118. In this embodiment, the distal tip 160 may serve as a third electrode, particularly if the probe shaft 136 is conductive. Alternatively, a third electrode array (not shown) may be carried on the distal tip 160 and deployed through the axial opening 118.

Significantly, because the inner and outer apertures 72, 74 alternate between open and closed positions, the cannula 102 may also be used to deliver other substances, such as a pharmaceutical agent, to a specific area. For example, the outer tube 66 may be translated to misalign the inner and outer apertures 72, 74, such that a pharmaceutical agent delivered to the cannula lumen 114 only deploys through the axial opening 118. If the cannula 102 only provided side slots but no mechanism to close the side slots, then it would be difficult to control deployment of the pharmaceutical agent, as the pharmaceutical agent could leak through the side slots as well as the axial opening 118. However, if a large distribution area for a substance is desired, then aligning the inner and outer apertures 72, 74 allows for distribution of the substance through the inner and outer apertures 72, 74 as well as the axial opening 118.

Figure 10A:
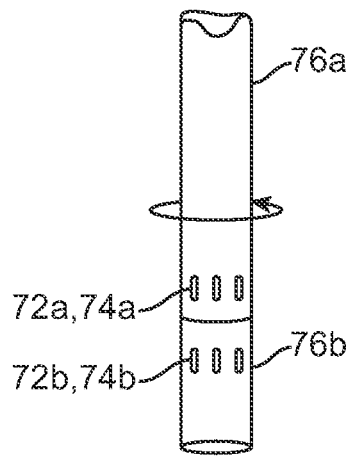
FIGS. 10A and 10B are side views of an alternative embodiment of the cannula in FIG. 1.
Figure 10B:
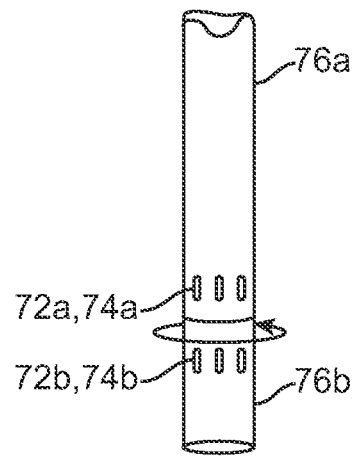

For more selective delivery of a pharmaceutical agent, an alternative embodiment of the cannula 102, shown in FIGS. 10A and 10B, includes a proximal portion 76a of the outer tube 68, on which the proximal outer apertures 74a are positioned, and a distal portion 76b of the outer tube 68, on which the distal outer apertures 74b are positioned. The proximal portion 76a and the distal portion 76b are separately translatable, such that the proximal inner and outer apertures 72a, 74a may be aligned while the distal inner and outer apertures 72b, 74b are misaligned (FIG. 10A), and vice-versa (FIG. 10B). This may be achieved by translating separate outer tubes (not shown) associated with each of the proximal and distal sections 76a, 76b, or by other extensions that may be carried on the proximal end 109 of the cannula. In this embodiment, a pharmaceutical agent may be delivered through either of the proximal inner and outer apertures 72a, 74a or the distal inner and outer apertures 72b, 74b by selectively translating the proximal portion 76a and the distal portion 76b.

In another alternative embodiment, the cannula 102 may have a closed end (not shown). This may be desired when only an ablation probe and a fluid, such as a pharmaceutical agent or a conductive fluid, need to be deployed through the cannula 102. In this manner, a fluid can be deployed through the proximal inner and outer apertures 72a, 74a and the distal inner and outer apertures 72b, 74b, resulting in a more circumferential distribution of the fluid. The closed-end cannula may further include an outer tube with separately translatable proximal and distal portions, similar to the embodiment shown in FIGS. 10A and 10B to deliver a fluid to a proximal or distal area of tissue relative to the cannula.

Referring back to FIG. 1, to provide RF energy during an ablation procedure, the RF generator 105 may be a conventional general purpose electrosurgical power supply operating at a frequency in the range from 300 kHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Corporation. Preferred power supplies are models RF-2000 and RF-3000, available from Boston Scientific Corporation.

Having described the structure of the tissue ablation device 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 11A:
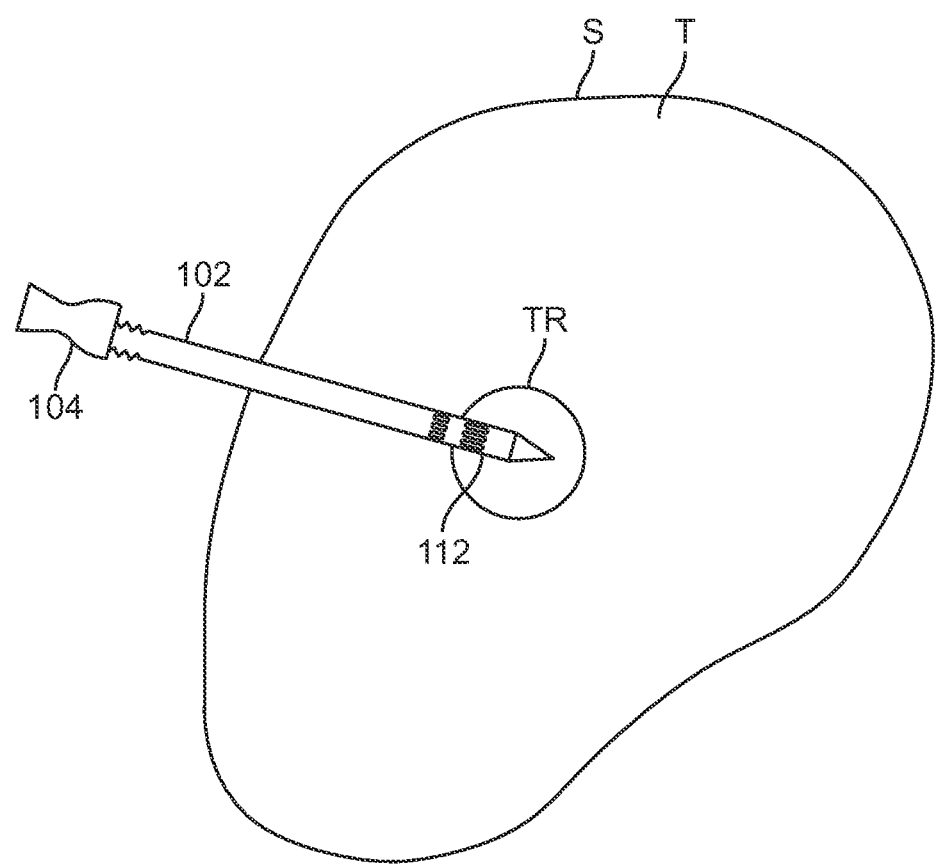
FIGS. 11A-11G are cross-sectional views of a method of using the tissue treatment device of FIG. 1 to treat tissue.

Referring now to FIGS. 11A-11G, the operation of the tissue ablation device 100 is described in treating a targeted tissue region TR within tissue T located beneath the skin or an organ surface S of a patient. For purposes of illustration, operation of only the embodiment shown in FIGS. 6A-6D will be described with reference to FIGS. 11A-11G. The delivery cannula 102 is first percutaneously introduced through the tissue T either directly through the patient's skin or through an open surgical incision, so that the distal end 112 of the delivery cannula 102 is located at the tissue region TR, and preferably in the center of the tissue region TR, as shown in FIG. 11A. This can be accomplished using any one of a variety of techniques. In the preferred method, the delivery cannula 102 is introduced through the tissue T, with the trocar 107 inserted into the cannula lumen 114 to form a mating arrangement with the delivery cannula 102. The sharpened distal tip of the trocar 107 facilitates introduction to the tissue region TR in this case. Alternatively, the delivery cannula 102 can be introduced through the tissue T, with the stylet 104 inserted into the cannula lumen 114 in a mating arrangement. In this case, the sharpened tip 130 of the stylet 104 facilitates introduction to the tissue region TR. Because the stylet 104 or trocar 107 are sufficiently rigid, i.e., have a sufficient column strength, the delivery cannula 102 need not be rigid, but instead can be flexible if desired. In any event, delivery cannula 102 can be properly positioned relative to the tissue region TR under ultrasonic or other conventional imaging.

Figure 11B:
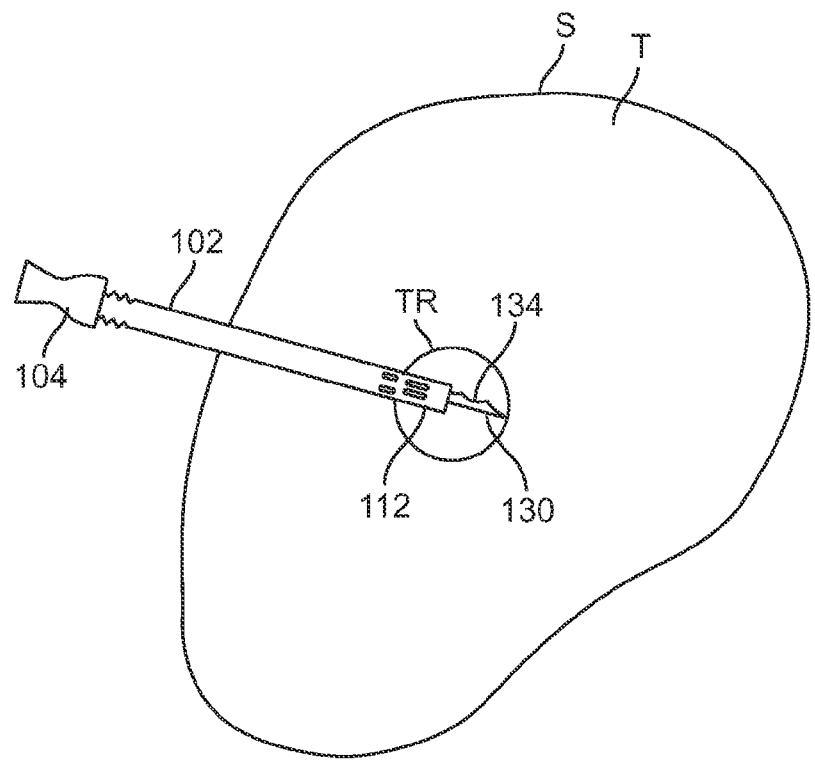

If the trocar 107, instead of the stylet 104, is used to introduce the delivery cannula 102 to the tissue region TR, the stylet 104 can be exchanged for the trocar 107. In particular, the trocar 107 is removed from the cannula lumen 114, and then the stylet 104 can be introduced into the cannula lumen 114, as illustrated in FIG. 11B. After the delivery cannula 102 is properly placed with the distal tip 130 of the biopsy stylet 104 deployed, a sample of the tissue region TR is obtained by distally advancing the delivery cannula 102 over the stylet 104 in order to shear off tissue within the notch 134. The stylet 104 is then removed from the cannula lumen 114 in order to retrieve the tissue sample for analysis in a laboratory. Of course, this is just one exemplary method of taking a tissue sample, and other conventional biopsy devices can be introduced through the cannula lumen 114 of the delivery cannula 102 in order to obtain a tissue sample.

Figure 11C:
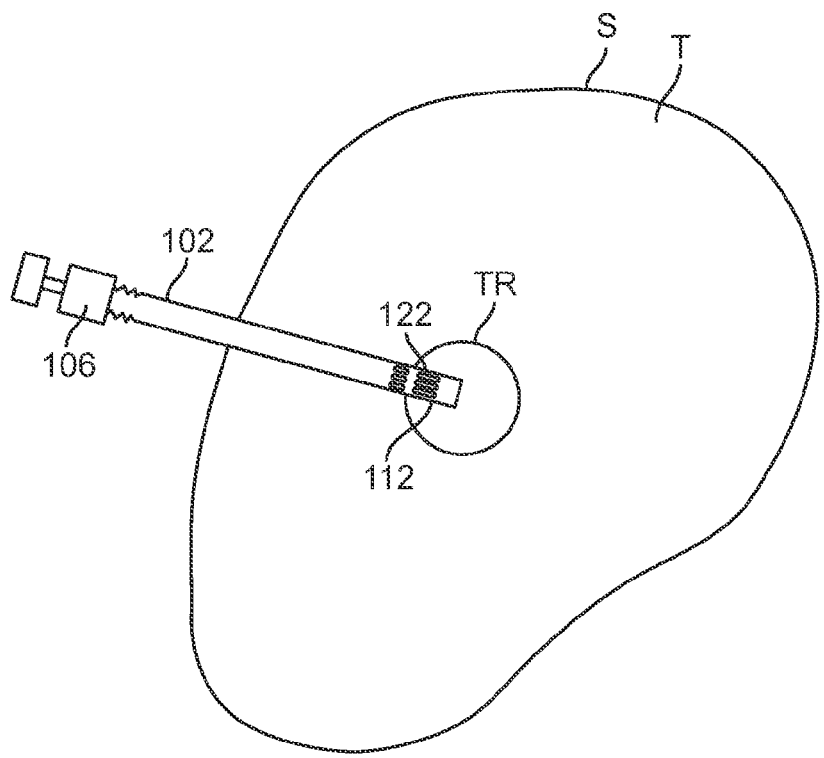

The ablation probe 106 is then introduced through the cannula lumen 114 in a mating arrangement with the delivery cannula 102 (FIG. 11C). The corresponding key slot (not shown) and key 151 (shown in FIG. 1) located on the respective ablation probe 106 and cannula 102 will circumferentially register the ablation probe 106 within the cannula lumen 114 to align the electrodes 138, 140 with the inner apertures 72a, 72b. In this manner, when the outer apertures 74a, 74b are respectively aligned with the inner apertures 72a, 72b, the tines 166 will be adjacent the inner apertures 72a, 72b and thus readily deployable through the inner 72a, 72b and outer 74a, 74b apertures.

After the probe 106 is introduced in the cannula 102, and if not already aligned, the outer tube 68 is rotationally translated to align the proximal inner and outer apertures 72a, 74a and the distal inner and outer apertures 72b, 74b. If the embodiment shown in FIGS. 8A-8D is alternatively used, the outer tube 66 may be proximally translated relative to the inner tube 64 to respectively align the proximal inner and outer apertures 72a, 74a and the distal inner and outer apertures 72b, 74b.

Figure 11D:
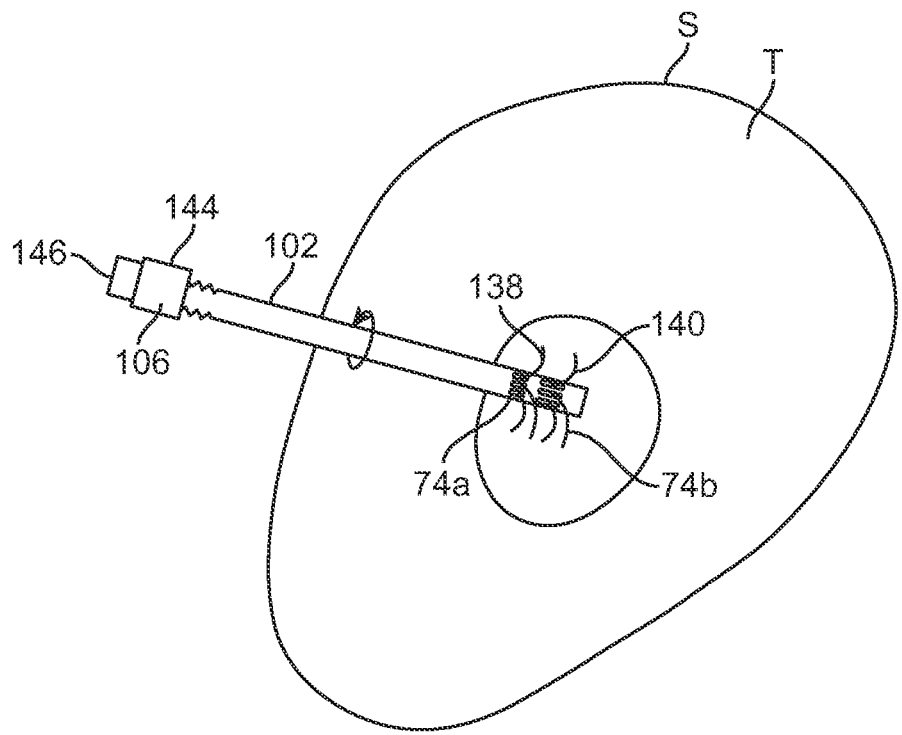

Next, the arrays 138, 140 are deployed from the ablation probe 106. In particular, as shown in FIG. 11D, the proximal array 138 is deployed through the aligned proximal inner and outer apertures 72a, 74a, and the distal array 140 is deployed through the aligned distal inner and outer apertures 72b, 74b. Alternatively, if the embodiment shown in FIG. 9A is used, the distal electrode array 140 is deployed through the axial opening 118. As can be seen, placement of the distal end 112 of the delivery cannula 102 at the center of the tissue region TR causes the distal electrode array 140 to be deployed into contact with the distal portion of the tissue region TR, and the proximal electrode array 138 to be deployed into contact with the proximal portion of the tissue region TR.

Figure 11E:
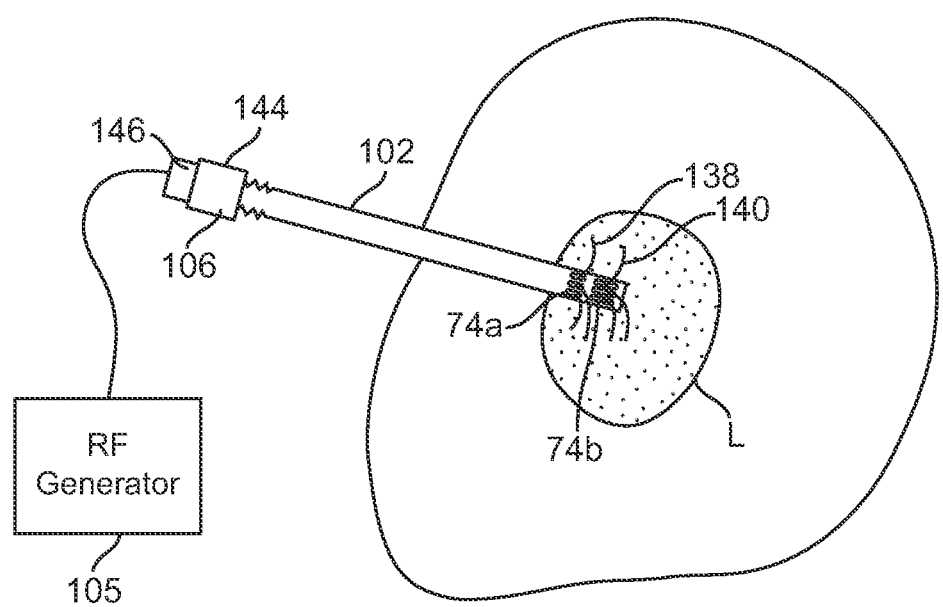

After the electrode arrays 138, 140 have been properly deployed into the tissue region TR, the RF generator 105 is connected to the electrical connector 148 located on the proximal handle member 146 (shown in FIG. 1), thereby connecting the respective electrodes arrays 138, 140 in a bipolar arrangement. Notably, the RF generator 105 may also be connected to the electrical connector 148 before deployment of the electrode arrays 138, 140. The RF generator 105 is then operated to ablate the tissue region TR. As a result of the ablation process, a lesion L will be created, which will eventually expand to include the entire tissue region TR (FIG. 11E).

Figure 11F:
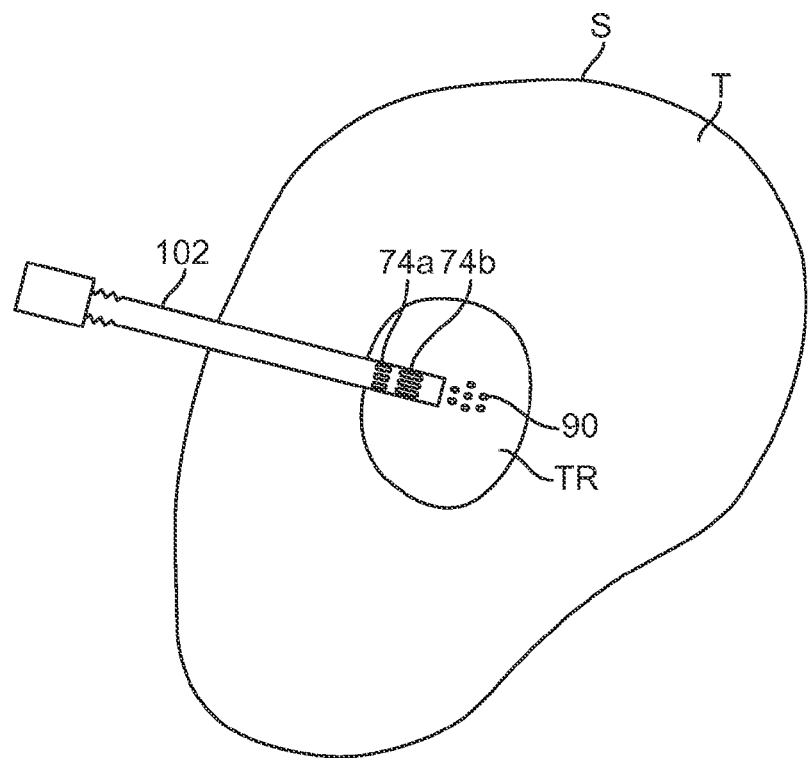
Figure 11G:
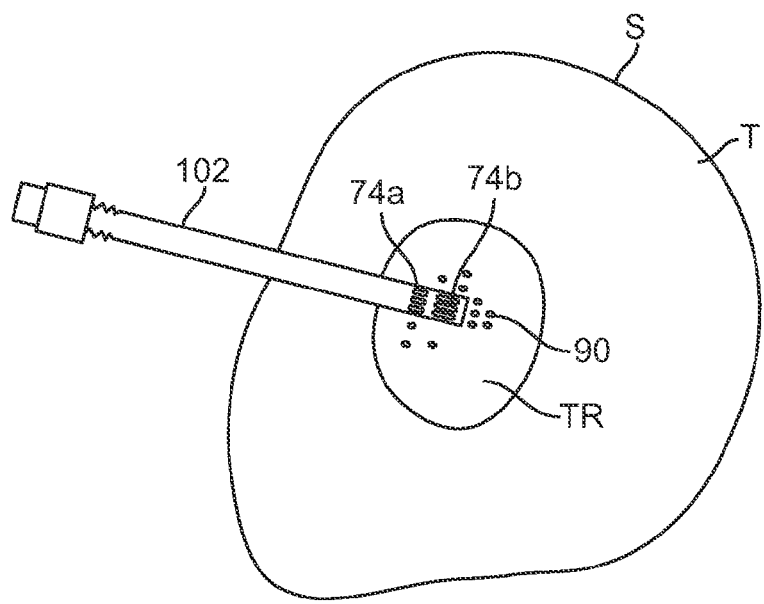

After the tissue region TR has been ablated, the electrode arrays 138, 140 are retracted, and the ablation probe 106 is removed from the cannula lumen 114 of the delivery cannula 102. The outer tube 66 may then be rotationally translated to respectively misalign the proximal inner and outer apertures 72a, 74a and the distal inner and outer apertures 72b, 74b. If the embodiment shown in FIGS. 8A-8D is alternatively used, the outer tube 66 may be distally translated relative to the inner tube 64 to respectively misalign the proximal inner and outer apertures 72a, 74a and the distal inner and outer apertures 72b, 74b. Next, one or more pharmaceutical agents 90 are introduced into the cannula lumen 114 for delivery to the tissue region TR through the axial opening 118, as shown in FIG. 11F. If desired, to increase the distribution area, the outer tube 68 is translated to align the proximal inner and outer apertures 72a, 74a and the distal inner and outer apertures 72b, 74b, such that the pharmaceutical agent 90 is delivered through proximal inner and outer apertures 72a, 74a and the distal inner and outer apertures 72b, 74b, in addition to the axial opening 118, as shown in FIG. 11G. This may be particularly desired for large ablation areas.

Figure 12A:
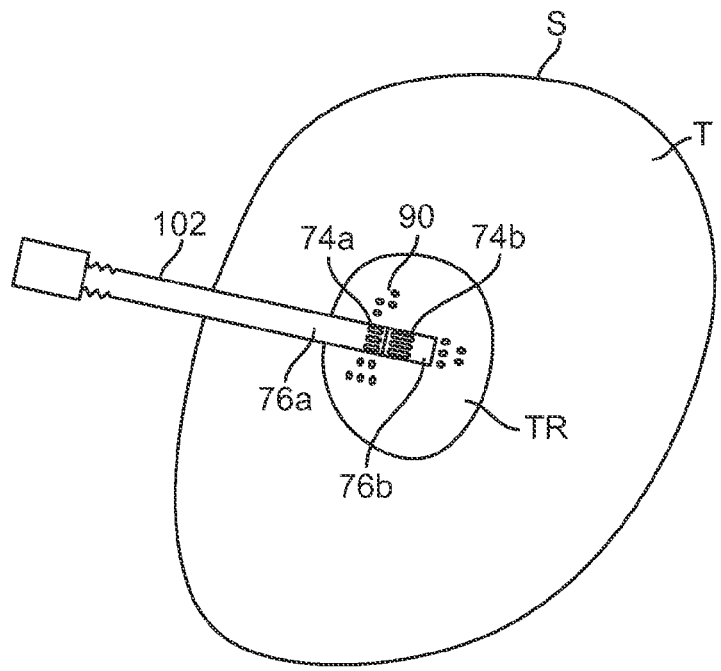
FIGS. 12A and 12B are cross-sectional views of a method of using the cannula of FIGS. 10A and 10B to deliver a pharmaceutical agent to target tissue.
Figure 12B:
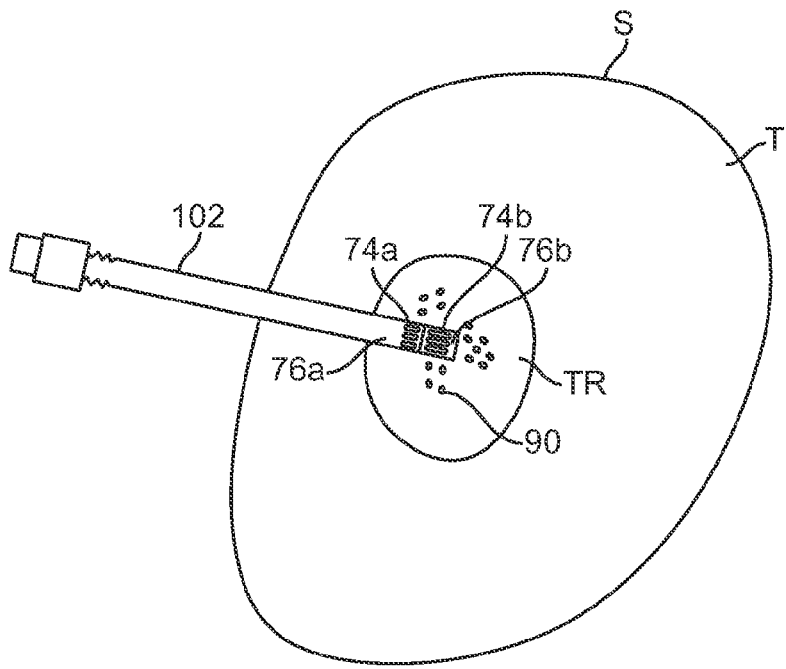

For more selective distribution of the pharmaceutical agent 90, the embodiment illustrated in FIGS. 10A and 10B can be used to distribute a pharmaceutical agent 90. The cannula 102 is inserted and the probe 106 is operated using the same steps described above. After the probe 106 is removed from the cannula 102, the proximal portion 76a and the distal portion 76b of the outer tube 76b are selectively translated to deliver the pharmaceutical agent 90. For example, in one method, the proximal portion 76a is translated to align the proximal inner and outer apertures 72a, 74b, while the distal inner and outer apertures 72b, 74b are misaligned, such that the pharmaceutical agent 90 is deployed through the proximal inner and outer apertures 72a, 74a and the axial opening 118, as shown in FIG. 12A. Alternatively, the distal inner and outer apertures 72b, 74b are aligned, while the proximal inner and outer apertures 72a, 74a are misaligned, such that the pharmaceutical agent 90 is deployed through the distal inner and outer apertures 72b, 74b and the axial opening 118, as shown in FIG. 12B. While these embodiments illustrate the pharmaceutical agent 90 only deploying through one of the proximal inner and outer apertures 72a, 74a or the distal inner and outer apertures 72b, 72b, the pharmaceutical agent 90 may also be deployed through both the proximal inner and outer apertures 72a, 74a and the distal inner and outer apertures 72b, 72b.

In the case where a closed-end cannula is used, the pharmaceutical agent 90 may be circumferentially delivered from the cannula lumen through the proximal inner and outer apertures 72a, 74a and the distal inner and outer apertures 72b, 74b to the target tissue region. For example, the pharmaceutical agent 90 may be delivered to the cannula lumen 114 and contained therein, until the distal end 111 of the cannula 102 is positioned at the desired site for delivering the agent 90. The outer tube 68 is then translated to align the proximal inner and outer apertures 72a, 74a and the distal inner and outer apertures 72b, 74b to deliver the pharmaceutical agent 90 to the target tissue region.

If the user wishes to deliver the pharmaceutical agent 90 to multiple tissue regions, the outer tube 68 is then misaligned before the entirety of the pharmaceutical agent 90 is delivered, such that a portion of the pharmaceutical agent 90 is retained in the cannula lumen 114. The cannula 102 is then manipulated from the proximal end 109, such that the distal end 111 is positioned at the next tissue region where the pharmaceutical agent 90 is to be delivered. The outer tube 68 is then translated to align the proximal inner and outer apertures 72a, 74a and the distal inner and outer apertures 72b, 74b to deliver the pharmaceutical agent 90 to the tissue region. This process may be repeated, and additional pharmaceutical agent 90 may be delivered to and retained in the cannula lumen 114, until the pharmaceutical agent 90 is delivered to all desired tissue regions.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A tissue ablation device, comprising:
    an ablation probe comprising an elongated probe shaft having a proximal end, a distal end, and a plurality of electrodes comprising a proximal electrode array and a distal electrode array carried on the elongated probe shaft distal end; and
    a cannula comprising:
        an elongated cannula shaft having a proximal end, a distal end, and concentric inner and outer tubes extending along a common longitudinal axis, wherein the inner and outer tubes are rotationally translatable about the longitudinal axis relative to each other, wherein the outer tube comprises a proximal portion and a distal portion, wherein the proximal portion is separately translatable from the distal portion,
        a lumen extending longitudinally within the elongated cannula shaft between the proximal and distal ends, wherein the cannula lumen is configured for removably receiving the elongated probe shaft,
        a plurality of proximal and distal inner apertures disposed transversely through a wall of the inner tube and in communication with the cannula lumen, and
        a plurality of proximal and distal outer apertures disposed transversely through a wall of the outer tube,
        wherein the proximal portion of the outer tube is configured for being translated to selectively align the proximal inner and outer apertures and misalign the proximal inner and outer apertures, wherein the distal portion of the outer tube is configured for being translated to selectively align the distal inner and outer apertures and misalign the distal inner and outer apertures, and wherein the proximal electrode array is deployable through the proximal inner and outer apertures when aligned, and the distal electrode array is deployable through the distal inner and outer apertures when aligned.

2. The tissue ablation device of claim 1, wherein the inner and outer tubes are configured for being longitudinally translated along the longitudinal axis relative to each other.

3. The tissue ablation device of claim 1, wherein the plurality of electrodes comprise sharpened distal tips.

4. The tissue ablation device of claim 1, wherein the plurality of inner and outer apertures are slots.

5. The tissue ablation device of claim 1, wherein the plurality of inner and outer apertures are substantially circular.

6. The tissue ablation device of claim 1, wherein the plurality of inner and outer apertures form a passageway angled relative to the longitudinal axis.

7. The tissue ablation device of claim 1, further comprising a handle assembly carried on the proximal end of the elongated probe shaft, the handle assembly comprising an electrical port coupling the plurality of electrodes to a source of electrical energy.

8. The tissue ablation device of claim 7, wherein the source of electrical energy is radio frequency (RF) energy.

9. A method for treating tissue using the tissue ablation device of claim 1, comprising:
introducing the cannula to a tissue site;
distally sliding the elongated probe shaft through the cannula lumen;
translating the proximal portion of the outer tube separately from the distal portion of the outer tube to align the proximal inner apertures with the proximal outer apertures;
translating the distal portion of the outer tube separately from the proximal portion of the outer tube to align the distal inner apertures with the distal outer apertures;
deploying the proximal array of electrodes through the proximal portion of the aligned inner and outer apertures;
deploying the distal array of electrodes through the distal portion of the aligned inner and outer apertures; and
operating the probe to ablate tissue by delivering electrical energy from the plurality of electrodes to the tissue site.

10. The method of claim 9, further comprising delivering a substance through the cannula lumen.

11. The method of claim 10, wherein the substance is a pharmaceutical agent.

12. The method of claim 10, further comprising translating the cannula outer tube such that the inner and outer apertures are misaligned prior to delivering the substance through the cannula lumen.

13. The method of claim 12 wherein the substance is delivered through an axial opening on the distal end of the elongated cannula shaft.

14. The method of claim 10, further comprising translating the cannula outer tube such that the inner and outer apertures are aligned prior to delivering the substance through the cannula lumen, and the substance is delivered through the inner and outer apertures and an axial opening on the distal end of the cannula shaft.

15. A cannula used in ablating tissue, comprising:
an elongated cannula shaft having proximal end, a distal end, and concentric inner and outer tubes extending along a common longitudinal axis, wherein the inner and outer tubes are rotationally translatable about the common longitudinal axis relative to each other, wherein the outer tube comprises a proximal portion and a distal portion, the proximal portion being separately translatable from the distal portion;
a lumen extending longitudinally within the elongated cannula shaft between the proximal and distal ends;
a plurality of proximal and distal inner apertures disposed transversely through a wall of the inner tube and in communication with the cannula lumen; and
a plurality of proximal and distal outer apertures disposed transversely through a wall of the outer tube,
wherein the proximal portion of the outer tube is configured for being translated to selectively align the proximal inner and outer apertures and misalign the proximal inner and outer apertures,
wherein the distal portion of the outer tube is configured for being translated to selectively align the distal inner and outer apertures and misalign the distal inner and outer apertures, and
wherein a plurality of electrodes is insertable through the lumen to be deployed through at least one of the aligned inner and outer apertures.

16. The cannula of claim 15, further comprising an axial opening on the distal end of the elongated cannula shaft.

17. The cannula of claim 15, wherein the inner and outer tubes are configured for being longitudinally translated along the longitudinal axis relative to each other.

* * * * *